United States Patent [19]
Mickle et al.

[11] Patent Number: 6,110,459
[45] Date of Patent: Aug. 29, 2000

[54] TRANSPLANTS FOR MYOCARDIAL SCARS AND METHODS AND CELLULAR PREPARATIONS

[76] Inventors: Donald A. G. Mickle, 7 McGillivary Ave., Toronto, Ont., Canada, M5M 2X9; Ren-Ke Li, 75 Ardgowan Oces, Scarborough, Ontario, Canada, M1V 1B4; Richard D. Weisel, 413 Sackville St., Toronto, Ontario, Canada, M4X 1S8

[21] Appl. No.: 08/863,882

[22] Filed: May 28, 1997

[51] Int. Cl.$^7$ .......................... A01N 63/00; A61K 38/18; C12N 5/02; C12N 5/06
[52] U.S. Cl. .................... 424/93.21; 424/85.1; 424/93.7; 435/325; 435/366; 435/371; 435/373; 435/374; 435/395
[58] Field of Search .............................. 424/93.2, 93.21, 424/93.3, 93.7, 85.1; 435/325, 366, 371, 373, 374, 395; 514/12, 21; 600/36

[56] References Cited

U.S. PATENT DOCUMENTS

| | | | |
|---|---|---|---|
| 5,199,942 | 4/1993 | Gillis | 604/4 |
| 5,202,120 | 4/1993 | Silver et al. | 424/93.7 |
| 5,580,779 | 12/1996 | Smith et al. | 435/378 |
| 5,602,301 | 2/1997 | Field | 800/2 |

FOREIGN PATENT DOCUMENTS

| | | |
|---|---|---|
| WO 95/12979 | 5/1995 | WIPO . |
| WO 95/14079 | 5/1995 | WIPO . |
| WO 95/34581 | 12/1995 | WIPO . |
| WO 96/38544 | 12/1996 | WIPO . |

OTHER PUBLICATIONS

Loer et al., "Transplantation of Fetal Myocardial Tissue Into the Infarcted Myocardium of Rat; A Potential Method for Repair of Infarcted Myocardium?" *Cell Transplants* 94:(Supplement II) II–332–II–336 (1996).

Murry et al., "Skeletal Myoblast Transplantation for Repair of Myocardial Necrosis" *J. Clin. Invest.* 98:2512–2523 (1996).

Chiu et al. Cellular Cardiomyoplasty: Mycardial Regeneration With Satellite Cell Implantation. Ann. Thorac. Surg. 60: 12–18, 1995.

Li et al.; Cardiomyocyte Transplantation Improves Heart Function; 1996 by the Society of Thoracic Surgeons; pp. 654–661.

Li et al.; Method of Culturing Cardiomyocytes from Human Pediatric Ventricular Myocardium; 1992 J. Tiss. Cult. Meth.; pp. 93–100.

Li et al.; Human Pediatric and Adult Ventricular Cardiomyocytes in Culture: Assessment of Phenotypic Changes with Passaging; Feb. 20, 1996 Cardiovascular Research; pp. 1–12.

*Primary Examiner*—Nancy Degen
*Attorney, Agent, or Firm*—Clark & Elbing LLP

[57] ABSTRACT

A method is provided for forming a graft in heart tissue which comprises the transplantation of cells chosen from cardiomyocytes, fibroblasts, smooth muscle cells, endothelial cells and skeletal myoblasts. The grafts are especially useful in treating scar tissue on the heart. Also provided is a method of isolating and culturing cardiomyocytes for use in such grafts.

45 Claims, 1 Drawing Sheet

TRANSPLANTS FOR MYOCARDIAL SCARS AND METHODS AND CELLULAR PREPARATIONS

FIELD OF THE INVENTION

The present invention relates to novel methods of cell transplantation into scar tissue in the heart in order to improve heart function, stimulate angiogenesis, and to salvage myocardium. The invention also relates to the preparation of culturing of the subject cells prior to transplantation, a mechanism for the delivery of gene therapy using such transplants and to grafts comprising such cells.

BACKGROUND OF THE INVENTION

Organ transplantation and surgical resection have been used to replace or remove diseased non-functional myocardial tissue. Recently fetal cellular transplantation has been used to improve neurological deficiencies found in Parkinson's disease (1). Normal myoblasts have been transplanted into the skeletal muscle of patients with Ducherne muscular dystrophy (2). The transplanted myoblasts expressed dystrophin. Fetal ventricular cardiomyocytes and skeletal myoblasts have been transplanted into normal myocardium by Loren Field (3, 4) U.S. Pat. No. 5,602,301). In these references, the cells were transplanted into the middle and thickest layer of the heart, composed of cardiac muscle, which has an excellent blood supply. The transplanted atrial tumor cells formed intercalated disc junctions with the host cardiomyocytes. Myocardial function measurements were not done. Since fetal ventricular cardiomyocytes and atrial tumor cells were successfully transplanted into the myocardium, it was assumed that adult ventricular cardiomyocytes could also be successfully transplanted. However, no evidence is provided that such transplantation would be successful in a damaged heart. We have shown that transplanted cells do not survive in necrosed myocardium because of the inflammatory response (Submitted to *Circulation Research*, not yet published). In addition to not demonstrating cell transplantation into damaged myocardium, Field does not teach the transplantation of cells into scar tissue.

Different from myocardial tissue, scar tissue in the heart has no cardiac muscle cells and is composed on connective tissue cells, such as fibroblasts, and non-cellular components, such as collagen and fibronectin. The scar tissue is formed after necrosing the ventricular wall of the heart. The mature scar tissue is though to be an inert tissue having a limited blood supply. Accordingly, from the prior art, it is not expected that cultured cells could be successfully transplanted into mature scar tissue.

Scar tissue is much thinner than normal myocardium. In accordance with the method taught by Field in U.S. Pat. No. 5,602,301, cellular grafts are introduced into the myocardium by injection. However, such method, if applied to the much thinner scar tissue, would result in a ballooning of such tissue and an accompanying increase in pressure within such area. In the result, the transplanted cellular material would leak from the puncture point of the injection needle upon withdrawal. Accordingly, the efficiency of such transplant procedure would be reduced.

Thus, there is a need to develop cellular allo- and autotransplantation technology in the scar tissue of the diseased myocardium to improve contractile function, to minimize myocardial remodeling, to stimulate angiogenesis, to deliver gene therapy, to rebuild the heart, and to salvage damaged cardiomyocytes. The present invention addresses these needs.

SUMMARY OF THE INVENTION

It is an object of the present invention to provide cell transplantation methods for treating scar tissue in the myocardium which overcome deficiencies in the prior art. The invention illustrates that atrial myocytes, smooth muscle cells, endothelial cells, and fibroblasts can be successfully transplanted into the scar tissue formed after ventricular necrosis and into tissue membranes and porous synthetic membranes. The cell grafts formed tissue which survived the 3 month duration of the study, improved myocardial function, limited myocardial remodeling, and stimulated angiogenesis. The presence of the grafts did no induce overt cardiac arrhythmias. When auto-cell transplantation occurred, immunorejection did not occur.

Accordingly, in one embodiment, the present invention provides a method of forming a stable myocardial graft in a mammal, the method comprising transplanting, in myocardial tissue or scar tissue in the heart, cell chosen from the group consisting of adult cardiomyocytes; fetal cardiomyocytes; adult fibroblasts; fetal fibroblasts; smooth muscle cells; endothelial cells; and skeletal myoblasts. In another embodiment, the invention provides for grafts of such cellular material either in solution or suspended on an appropriate scaffolding.

In a further embodiment, the invention provides a method of culturing cardiomyocytes from pediatric mammalian myocardial tissue comprising:

a) comminuting the myocardial tissue;

b) digesting the tissue for 15 minutes in a digesting solution containing 0.2% trypsin and 0.1% collagenase dissolved in phosphate buffered saline and separating the digested tissue solution;

c) adding to the digested tissue solution a culture medium comprising Iscove's modified Dulbecco's medium (IMDM), 10% fetal bovine serum, and 0.1 mM β-mercaptoethanol; the culture medium being added in a ratio of 20 volumes of culture medium to 1 volume of the digesting solution;

d) centrifuging the resulting solution at 581×g for 5 minutes and discarding the supernatant;

e) re-suspending the pellet in fresh culture medium;

f) culturing the suspension in 10% fetal bovine serum and 0.1 mM β-mercaptoethanol; and, g) isolating cardiomyocytes from the culture.

In yet another embodiment, the invention provides for a method of culturing adult cardiomyocytes which involves a second digestion step. The invention further provides for methods of passaging and storing the cultured cardiomyocytes. The invention also provides a method of treating defective, damaged or scarified heart tissue with the above mentioned grafts.

BRIEF DESCRIPTION OF THE DRAWINGS

These and other features of the present invention will become more apparent in the following detailed description wherein references are made to the following FIGURE.

DETAILED DESCRIPTION OF THE PREFERRED EMBODIMENTS

Figure 1:
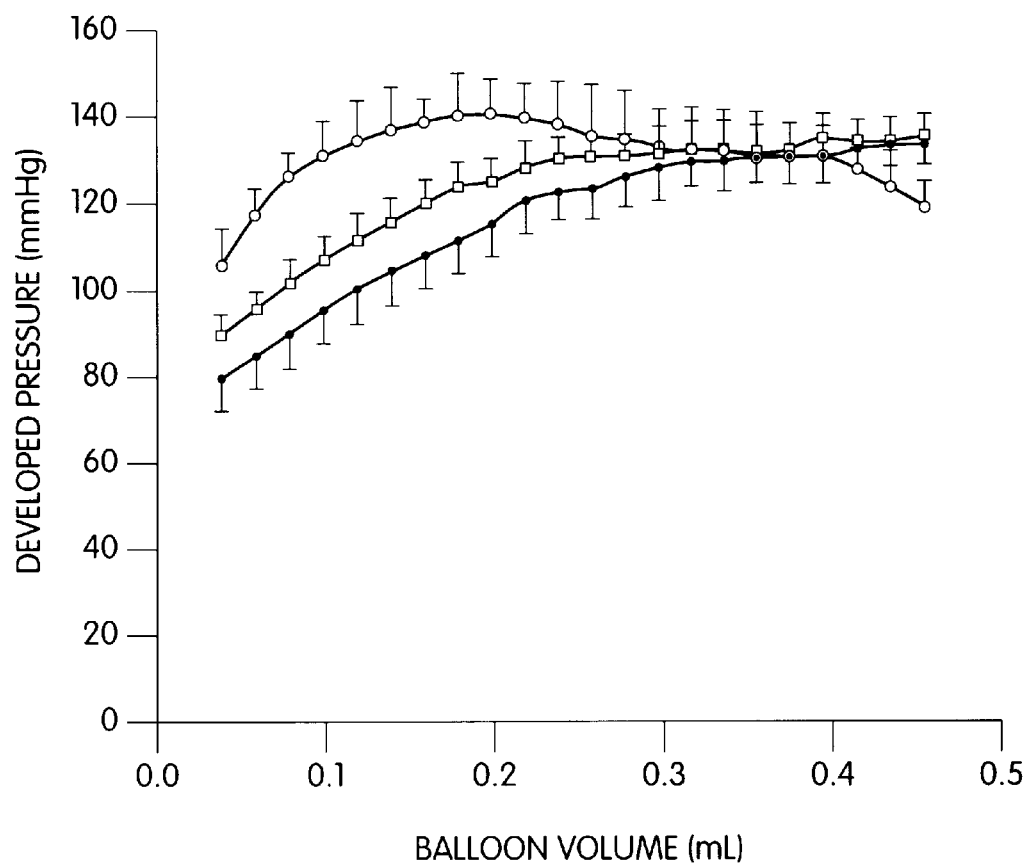
FIG. 1 illustrates the improvement in myocardial function with the cell transplantation method of the present invention.

In investigating the use of grafts, comprising cellular transplants, in treating scar tissue in the heart, the present inventors transplanted cultured cells into the center of a mature ventricular scar so that there was no contact between the transplanted cells and the host cells. Such methodology was followed to aid in the identification of the transplant. Initially, in transplanting fetal cardiomyocytes into the mature scar, it was surprising to find a stimulation of angiogenesis in the affected area and an improvement in heart function. Since we were unsuccessful in transplanting adult ventricular cardiomyocytes into myocardial scar tissue despite success with fetal ventricular cardiomyocytes, we were surprised that adult atrial cardiomyocytes could be successfully transplanted into such scar tissue. In further studies, we have transplanted auto- and allo-smooth muscle cells, fibroblasts, and endothelial cells into the center of a mature ventricular scar. As with our previous findings, the cell transplants formed stable grafts in the scar, improved myocardial function, decreased myocardial remodeling, stimulated angiogenesis, salvaged myocardium, and provided a means of gene delivery. On the basis of these studies we expect that similar results can be obtained from the use of skeletal myoblasts as well.

The present invention have also developed a novel method of culturing, passaging and storing adult human ventricular cardiomyocytes. Culturing of adult cardiomyocytes permits an opportunity to restore function and blood flow to regions of the heart which were destroyed by acquired heart disease or absent because of congenital heart disease. The adult cardiomyocyte cell culture method permits an opportunity to test a variety of pharmacological and mechanism inventions to prevent or ameliorate cardiac damage during cardiac surgery. Therefore, this unique method offers the promise of preventing injury as well as restoring heart function after cardiac injury.

The following examples will assist those skilled in the art to better understand the invention and its principles and advantages. It is intended that these examples be illustrative of the invention and not limit the scope thereof.

A. METHODS

EXAMPLE 1

Cell Isolation, Culture and Identification

The following procedures were approved by the hospital's Experimentation Committee.

1. Fetal Cardiomyocyte Culture: Fetal rat cardiomyocytes were isolated using an enzymatic digestion method (5,6) from 18-day gestational Sprague-Dawley rat heart ventricles (Charles River Canada Inc. Quebec, Canada). Fetal rats were anesthetized with intraperitoneal injection of sodium pentobarbital (30 mg/kg) and the hearts were then excised. The heart tissues were washed with phosphate-buffered saline (NaCl 136.9 mM, KCl 2.7 mM, $Na_2HPO_4$, 8.1 mM $KH_2PO_4$ 1.5 mM pH 7.3). The tissues were minced and incubated in 10 ml phosphate buffered saline containing 0.2% trypsin, 0.1% collagenase, and 0.02% glucose for 30 minutes at 37° C. The cardiomyocytes were then isolated by repetitive pipetting of the digested myocardial tissue. The cells in the supernatant were transferred into a tube containing 20 ml of cell culture medium (Iscove's modified Dulbecco's medium containing 10% fetal bovine serum, 0.1 mmole/L β-mercaptoethanol, 100 units/ml penicillin and 100 ug/ml streptomycin). The tube was centrifuged at 600×g for 5 minutes at room temperature and the cell pellet was resuspended in the cell culture medium for purification.

2. Adult Ventricular Cardiomyocyte Culture: Adult rat (Charles River Canada Inc. Quebec, Canada) were anesthetized with intramuscular administration of ketamine hydrochloride (22 mg/kg body weight) followed by an intraperitoneal injection of sodium pentobarbital (30 mg/kg) and the hearts were then excised. Cardiomyocytes were isolated by enzymatic digestion as described in Section 1. Adult human ventricular biopsies obtained from the operating theatre were similarly enzymatically digested.

3. Adult Atrial Cardiomyocyte Culture: The 400 g rat (Charles River Canada Inc. Quebec, Canada) were anesthetized similarly to Section 2. The atrial appendages was ligated and removed. The adult animals were survived. The atrial tissue was used for cardiomyocytes isolation as described in Section 1. Adult human atrial tissue was obtained from the operating theatre and similarly enzymatically digested.

4. Fetal Smooth Muscle Cells: Fetal rat smooth muscle cells were isolated using an enzymatic digestion method (7) from 18-day gestational Sprague-Dawley rat stomachs (Charles River Canada Inc. Quebec, Canada). Fetal rats were anesthetized with pentobarbital (30 mg/kg body weight, intraperitoneal) and the stomachs were then excised. The stomachs were washed with phosphate buffered saline. The stomachs were minced and incubated in 10 ml phosphate buffered saline containing 0.2% trypsin, 0.1% collagenase, and 0.02% glucose for 30 minutes at 37° C. The smooth muscle cells were isolated by repetitive pipetting of the digested myocardial tissue. The cells in the supernatant were transferred into a tube containing 20 ml of cell culture medium (199 medium containing 20% fetal bovine serum, 100 unites/ml penicillin and 100 ng/ml streptomycin). The tube was centrifuged at 600×g for 5 minutes at room temperature and the cell pellet was resuspended in the cell culture medium and cultured.

5. Adult Smooth Muscle Cells: Adult female rats (Charles River Canada Inc. Quebec, Canada) were anesthetized as described in Section 2. Uterus was removed after occlusion of blood vessel and incision was closed. The smooth muscle cells were isolated from uterus as described in Section 4.

6. Fetal Fibroblasts: Fetal rat skin biopsies were obtained from 18-day gestational Sprague-Dawley rat when the rats were anesthetized. Fibroblasts from fetal rat skin were isolated, purified and cultured as previously described (8). Briefly, the tissue was washed with phosphate buffered saline and minced. The tissue was then digested with in 10 ml phosphate buffered saline containing 0.2% trypsin, 0.1% collagenase, and 0.02% glucose for 30 minutes at 37° C. The fibroblasts were isolated by repetitive pipetting of the digested myocardial tissue. The cells in the supernatant was transferred into a tube containing 20 ml of cell culture medium (Dulbecco's Modified Essential Medium containing 10% fetal bovine serum, 100 units/ml penicillin and 100 ug/ml streptomycin). The tube was centrifuged at 600×g for 5 minutes at room temperature and the cell pellet was resuspended in the cell culture medium and cultured.

7. Adult Fibroblasts: Skin biopsies were obtained from adult Sprague-Dawley rats when the rats were anesthetized. The fibroblasts were isolated and cultured as described in Section 6.

8. Adult Endothelial Cells: Adult rat vascular endothelial cells were isolated using an enzymatic digestion method (8) from Sprague-Dawley rat aorta (Charles River Canada Inc. Quebec, Canada). Adult rats were anesthetized as described in Section 2. The aorta was then excised, washed with phosphate buffered saline and incubated in 10 ml phosphate buffered saline containing 0.2% trypsin, 0.1% collagenase, and 0.02% glucose for 30 minutes at 37° C. The blood vessel was washed with cell culture medium (199 medium containing 20% fetal bovine serum, 100 units/ml penicillin and 100 ug/ml streptomycin). The endothelial cells were cultured.

9. Human Cell Isolation, Culturing and Storage: Human cardiomyocytes were isolated from atrial appendages and ventricular myocardial biopsies obtained from patients undergoing corrective cardiac surgery. Human myocardium was dissected to remove connective tissue and then minced to pieces less than 1 mm$^3$ in size.

9(a). Pediatric Cardiomyocytes: Pediatric tissue was digested in an enzymatic digestion solution containing 0.2% trypsin, 0.1% collagenase dissolved in phosphate-buffered saline for 15 minutes. No calcium or EDTA was added. Culture medium containing Iscove's modified Dulbecco's medium (IMDM), 10% fetal bovine serum and 0.1 mM β-mercaptoethanol was added in a ratio of 20 volumes culture medium to 1 volume enyzmatic digestion solution. The solution was centrifuged at 581 g for 5 minutes. The supernatant was discarded. The cell and tissue pellet was resuspended in culture medium. The isolated cells were cultured on a dish for 5 to 8 days. Cardiomyocytes which migrated from this culture were collected by a Pasteur pipette and cultured.

9(b). Adult Cardiomyocytes: Different from pediatric tissue digestion, adult human myocardium was digested twice. The second digestion was necessary for the adult tissue due to the increased amount of corrective tissue. After the tissue was digested as described above, the solution containing suspended cells was collected. The remaining tissue was incubated with the enzymatic solution for a second time for 10 minutes and the cell suspension was collected. The two collected suspensions were combined. After centrifugation, the cell pellet was resuspended and cultured. The digested tissue fragments in the pellet were collected and cultured for no longer than 2 days (to avoid cell deterioration) and a further enzymatic digestion carried out on the remaining undigested tissue if sufficient cells were not found in the suspensions. Cardiomyocytes were found to grow from the cultured tissue fragments. The cells were isolated and then cultured.

9(c). Passaging of Culture: The cardiomyocytes were cultured in a medium containing IMDM, 10% fetal bovine serum and 0.1 mM β-mercaptoethanol. The cells were subcultured when the culture reached confluence (i.e. when the cell culture covered the dish surface and the cells began contacting each other). If the cells were subcultured before reaching confluency, the cells would undergo de-differentiation quickly. De-differentiated cells cannot be successfully transplanted. If the cells were allowed to become over-confluent, enzymatic digestion yielded cell clumps which would not dissociate. The cardiomyocytes in the cell clumps would not divide in culture. The subculturing enzymatic solution contained 0.01% trypsin, 0.02% glucose and 0.5 mM EDTA.

9(d). Storage of Cultured Cells: The primary cultures of human cardiomyocytes were stored for future use in liquid nitrogen. The cultured cardiomyocytes were dissociated from the culture plate using the subculturing enzymatic digestion solution. Culture medium was added in a ratio of 5 volumes culture medium to 1 volume digestion solution. The resultant solution was centrifuged at 581 g for 5 minutes. The supernatant was removed and the cell pellet was gently re-suspended in 1 mL IMDM containing 20% fetal bovine serum and 20% glycerol. The solution was transferred to a sterile cryo-vial in a Nalgene freezing container containing isopropranol in its base. The container was stored in a −80° C. freezer container for a period of time that: (a) ensured that the cells reached −80° C.; and (b) prevented over oxidation of the cells. In the present example, the container containing the solution was stored for a minimum of 4 hours and no longer than 8 hours. The long term storage of the cryo-vials containing the cells was in liquid nitrogen.

9(e). Thawing of Culture: When the stored cells were to be cultured, the vial was removed from liquid nitrogen and warmed at 37° C. Although 37° C. was found to be preferred, thawing of the cells may take place at other temperatures which allow for rapid yet non-destructive warming. The initial plating of the cells was done in 10 mL of IMDM medium containing 20% fetal bovine serum. The cells are kept in this warming medium for 3 to 5 days to allow the cells to attach firmly to the culture dish before switching to the usual culture medium. The warming medium needs to contain IMDM and 20% fetal bovine serum, the human cardiomyocytes will not divide and will de-differentiate. De-differentiated cardiomyocytes cannot be used for transplantation. The cardiomyocytes, cryo-frozen and warmed as described, were morphologically identical to cells which had not been frozen and were successfully subcultured. Frozen and unfrozen cells were collected and analyzed for mitochondrial integrity at each passage for 7 passages (in one month of subculture following thawing and plating). The mitochondrial enzyme cytochrome C oxidase showed no difference in activity between frozen and unfrozen cardiomyocytes at each passage. The technique to freeze and then re-survive cardiomyocytes is an important technique since the "life-time" of primary human cardiomyocytes cultures can now be extended.

9(f). Endothelial Cells: Human vascular endothelial cells were isolated from saphenous vein and aorta obtained from patients undergoing coronary bypass surgery. The endothelial cells were isolated as described in Section 8.

9(g). Smooth Muscle Cells: Human smooth muscle cells were isolated from saphenous vein after endothelial cell isolation. After endothelial cells were washed out as described in Section 8, the tissue was minced and incubated in 10 ml phosphate buffered saline containing 0.2% trypsin, 0.1% collagenase, and 0.02% glucose for 30 minutes at 37° C. The smooth muscle cells were isolated by repetitive pipetting of the digested tissue. The cells in the supernatant were transferred into a tube containing 20 ml of cell culture medium (199 medium containing 20% fetal bovine serum, 100 units/ml penicillin and 100 ug/ml streptomycin). The tube was centrifuged at 600×g for 5 minutes at room temperature and the cell pellet was resuspended in the cell culture medium and cultured.

9(h). Fibroblasts: Human fibroblasts were isolated from skin biopsies as described in Section 6.

10. Cell Purification: The isolated cardiomyocytes, smooth muscle cells, vascular endothelial cells were purified by a preplating technique (9), which takes advantage of the finding that these cells require a longer time to attach to a cell culture dish than fibroblast cells. The freshly isolated cells were plated on dishes and cultured for 2 hours at 37° C. The supernatant containing the suspended cells was transferred into another dish for further culturing.

The other technique used was the clonal dilution technique. When the cells are seeded at low density for culturing, vial cells form individual colonies. If any cell not of the type to be cultured is adjacent to a colony of interest it is necrosed with a sterile needle. At this time colonies can be picked up using a sterile Pasteur pipette and transferred to new culture dishes for culturing and passaging.

The human cardiomyocytes were not purified by the preplating technique nor by the clonal dilution technique when cultured and passaged. The adult cells were not seeded at low density to optimize the number of viable cardiomyocytes available to be cultured.

11. Cell Identification: Cardiomyocytes: The purity of cultured cardiomyocytes was assessed by immunofluorescent staining for cardiac myosin heavy chain (Rougier Bio-Tech Ltd, Quebec) (10). The cultured cells were fixed with methanol at $-20°$ C. for 15 minutes, washed with phosphate buffered saline, incubated with a monoclonal antibody against MHC for 45 minutes at 37° C., washed three times with phosphate buffered saline for 5 minutes each at room temperature, and then under humid and dark conditions incubated with rabbit anti-mouse IgG conjugated with fluorescein isothiocyanate for 45 minutes at 37° C. The cells were washed with phosphate buffered saline, mounted and photographed using a light and UV microscope. The cardiomyocyte purity was determined by counting the percentage of stained cells in 8 random fields/dish. Eight dishes of cardiomyocyte cultures were used in each cardiomyocyte preparation.

Smooth Muscle Cells: The purity of smooth muscle cell culture was determined by immunofluorescent staining for α-smooth muscle cell actin (Sigma) as described in last paragraph.

Vascular Endothelial Cells: The purity of endothelial cell culture was determined by immunofluorescent staining for factor VIII as described in cardiomyocyte section.

Fibroblasts: The purity of fibroblast cell culture was determined morphologically under microscope.

EXAMPLE 2

Cell Transplantation

In the examples, the subject animals were grouped into three categories, namely, sham, control and transplantation. The criteria for such grouping was as follows:

| Group | Surgical exposure | Scar generation | Cell transplantation |
|---|---|---|---|
| Sham | X | | |
| Control | X | X | |
| Transplantation | X | X | X |

1. Surgical Exposure: Sprague-Dawley rats (500 gram) were anesthetized with ketamine (22 mg/kg body weight, intramuscular) followed by an intraperitoneal injection of pentobarbital (30 mg/kg body weight). Once anaesthetized, rats were intubated and positive pressure ventilation maintained with a Harvard ventilator (Model 683, USA). The respiratory rate was set at 60 cycles/minute with a tidal volume of 2 ml. Animals were ventilated with oxygen supplemented room air. The heart was exposed through a 2 cm left lateral thoracotomy. The muscle layer and skin incision were surgically closed with 5-0 vicryl sutures.

2. Myocardial Injury and Myocardial Scar Generation: The hearts of the adult rats was exposed as described in SECTION 1. A 5 mm diameter metal probe cooled to—190° C. for 2 minutes was applied to the left ventricular free wall of the heart of 20 seconds. This procedure was repeated 8 times. The muscle layer and skin incision were then surgically closed with 5-0 vicryl sutures.

The animals recovered from surgery in a warm environment, were monitored for 4 hours postoperatively and then given Penlog XL (benzathine penicillin G 150,000 U/ml and procaine penicillin G 150,000 U/ml) intramuscularly (0.25 ml/rat) every three days, and buprenorphine (0.02–0.05 mg/kg body weight) subcutaneously 8–12 hourly for the first 48 hours following surgery.

3. Transfection of the Cultured Cardiomyocytes: Freshly isolated or cultured cells were transfected by calcium phosphate coprecipitation technique (11) with plasmid containing β-galactosidase gene. Plasmid DNA (20 ug) dissolved in 450 μl of sterile water and 50 μl of 2.5 M $CaCl_2$ was slowly added to 500 μl of aerated 2 X HEPES-buffered saline (0.284 M NaCl, 0.050 M HEPES acid, and 1.48 mM $Na_2HPO_4$ pH 7.05). After 20 minutes at room temperature, the resultant solution was added to the cardiomyocyte suspension ($1.0\times10^6$ cells/6 ml of culture medium). In the control groups the same procedure was performed without plasmid DNA and with pREP4 (a plasmid without the β-galactosidase gene from Invitrogen, USA) (plasmid control). The cells were cultured at 37° C., 5% $CO_2$ and 95% air for 24 hours.

To determine the efficiency of cell transfection, cells cultured for 24 hours and 4 weeks were washed three times with phosphate buffered saline, fixed in 2% formaldehyde and 2% glutaraldehyde in phosphate buffer (0.15 M NaCl and 0.015 M $NaH_2PO_4$, pH 7.2) at 4° C. for 5 minutes, washed with phosphate buffer containing 2.0 mM $MgCl_2$, and stained overnight at 37° C. in a solution containing 1 mg/ml 5-bromo-4-chloro-3-indolyl-beta-galactopyranoside (X-gal), 5 mM $K_3Fe(CN)_6$, 5 mM $K_4Fe(CN)_6 3H_3O$, 0.2 mM $MgCl_2$ in phosphate buffer (pH 7.2). The stained and non-stained cells in 8 random fields/dish (6 dishes from 6 preparations) were counted under the microscope to determine the percentage of cells containing β-galactosidase activity. Two dishes from each transplant experiment were used for a cell transfection efficiency study (N(number of animals)=6).

4. Cell Preparation and Transplantation: Cultured cells were washed three times with phosphate buffered saline to remove dead cells and then detached from the cell culture dish and each other with 0.05% trypsin in phosphate buffered saline for 3 minutes. After adding 10 ml of cultured medium, the cell suspension was centrifuged at 580×g for 3 minutes. The cell pellet was resuspended in culture medium at a concentration of $4\times10^5$ cells/ml culture medium. The volume of cell suspension was 0.25 ml for each cell transplantation.

On day 14 or 30 following surgery, a mature transmural scar was formed in the ventricle. The animals were anesthetized as described in Section 1. The scar tissue in the heart was exposed through a midline sternotomy. The cell suspension (0.25 ml) was injected into the scar tissue using a tuberculin syringe in the animals of transplanted group. Control animals were similarly injected with 0.25 ml of culture medium. The rats in the sham group underwent the same procedure without injection. Cryo-precipitate was put on the injection sites to prevent leakage of the injected cells. The chest was closed with 5-0 vicryl sutures. Antibiotics and analgesia were given as described in Section 1. Cyclosporin A, at a dose of 5 mg/kg body weight/day, was administered subcutaneously into animals of all three groups. The rats were housed in cages with filter tops.

EXAMPLE 3

Heart Function

At 8-weeks after myocardial injury, the heart function of sham, control and transplanted animals was measured using a Langendorff preparation [12]. The rats were anesthetized and heparin (200 units) was administered intravenously. The hearts were quickly isolated from rats and perfused in a Langendorff apparatus with filtered Krebs Heinseleit buffer (mmol/L NaCl 118, KCl 4.7, $KH_2PO_4$ 1.2, $CaCl_2$ 2.5, $MgSO_4$ 1.2, $NaHCO_3$ 25, glucose 11; pH 7.4) equilibrated with a 5% $CO_2$ and 95% $O_2$. A latex balloon was passed into the left ventricle through the mitral valve and connected to a pressure transducer (Model p10EZ, Viggo-Spectramed, CA) and transducer amplifier an differentiator amplifier (Model 11-G4113-01, Gould Instrument System Inc., Ohio). After 30 minutes of stabilization, the coronary flow of the heart was measured in triplicate by timed collection in the emptying beating state. The balloon size was increased by addition of saline in 0.02 ml increments from 0.04 to 0.8 ml, or the volume at which end diastolic pressure reaches to 30 mm Hg or which came first. The systolic and diastolic pressures were recorded at each balloon volume and developed pressure was calculated as the difference between the systolic and diastolic pressures.

The heart was weighed and the size measured by water displacement.

EXAMPLE 4

Measurement of Left Ventricular Remodeling

The epicardial and endocardial surface areas of the normal and scar tissue in the left ventricular free wall (LVFW) were measured by the techniques of Pfeffer et al (13) and Jugdutt and Khan (14). Briefly, the hearts were fixed in distension (30 mm Hg) with 10% phosphate-buffered formalin solution and then cut into 3 mm thick sections. For each section, the area of normal tissue, scar tissue, and transplanted tissue in the left ventricular free wall were traced onto a transparency and quantified using computerized planimetry (Jandal Scientific Sigma Scan, USA) as described by Wu et al. (15). The lengths of left ventricular free wall and scar tissue on both the endocardial and epicardial surfaces of each section were measured. The surface areas of the epicardial and endocardial scar tissue and left ventricular free wall were measured as:

(endocardial length+epicardial length)×section thickness (3 mm).

The surface area percentage of scar tissue in the left ventricular free wall (LVFW) was calculated as:

$$\frac{(\text{epicardial scar size} + \text{endocardial scar size})}{(\text{endocardial } LVFW1 + \text{epicardial } LVFW)} \times 100.$$

To calculate the percentage of the surface area in the scar tissue occupied by the transplanted tissue, the following equation was used:

$$\frac{(\text{cardiac tissue length in the scar tissue of each section}) \times (\text{section thickness (3 mm)})}{(\text{total scar area})} \times 100$$

EXAMPLE 5

Histology and Electron Microscopy of Transplanted Cells

On day 30 or 45 post-transplantation, the animals were anesthetized as in Example 1 and transplant, control, and sham hearts were exposed through a midline sternotomy and quickly harvested. The animals were euthanised by exsanguination under general anesthesia.

To localize the tissue formed by transplanted cells, the transplanted and control myocardial scar tissue were fixed in 5% glacial acetic acid in methanol. The tissue was embedded in paraffin and sectioned into 10 μm thick slices. After removal of the paraffin by immersing the slices for 3 minutes in xylene and then in 100, 95, 90, 85, and 70% ethanol for 3 minutes each, the samples were stained with haematoxylin and eosin as described in the manufacturer's specification (Sigma Diagnostics, St. Louis, Mo.), and photographed.

To stain for β-galactosidase activity in the transplanted cardiomyocytes, the heart sections were fixed in 2% formaldehyde and 2% glutaraldehyde in phosphate buffer (0.15 M NaCl and 0.015 M $NaH_2PO_4$, pH 7.2) at 4° C. for 12 hours. The transplanted cardiomyocytes were localized by staining for β-galactosidase activity as described earlier in Example 2. The stained tissue was embedded in paraffin and sectioned into 10 μm thick slices which were stained with haematoxylin and eosin as described in last paragraph.

To identify cultured ventricular and atrial cardiomyocyte transplants, the tissue was immunofluorescently stained for cardiac myosin heavy chain. Briefly, the tissues were sectioned and the tissue slices were washed three times with phosphate buffered saline and fixed with 2 ml 100% cold methanol at −20° C. for 15 minutes. After washing three times with phosphate buffered saline and drying by draining, the tissues were exposed to monoclonal antibodies against cardiac myosin heavy chain (Rougier Bio-Tech, Montreal, Canada), at concentration of 1:20 dilution with saline, for 45 minutes at 37° C. The control tissues were incubated with phosphate buffered saline under the same conditions. The tissues were washed three times with phosphate buffered saline for 15 minutes at room temperature with gentle shaking. The secondary antibody, rabbit anti-mouse IgG conjugated with fluorescein isothiocyanate at a concentration of 1:32 dilution with phosphate buffered saline, was added. The tissues were incubated with the second antibody under dark and humid conditions for 45 minutes at 37° C. After washing with phosphate buffered saline, the cells in the transplant control tissues were visualized under ultraviolet light using an epi-microscope with a blue filter.

The smooth muscle cell transplants were immunofluorescently stained using a monoclonal antibody for α-smooth muscle actin as the primary antibody. Similarly the endothelial cells were identified by immunofluorescent staining for factor VIII.

The fibroblast transplants were identified by the presence of a localized immunorejection within the ventricular scar.

EXAMPLE 6

Histological and Electron Microscopy Studies of Angiogenesis in the Graft

For immunocytochemical staining of factor VIII-related antigen in the vascular endothelial cells, sample slices processed in Example 5 were incubated with xylene twice for 5 minutes each, 100% ethanol twice for 2 minutes each and then with 70% ethanol twice for 1 minute each. The slices were incubated with rabbit IgG against factor VIII-related antigen (Dimension Lab, Inc. Ontario). The control samples were incubated with phosphate buffered saline under the same conditions. The test and control samples were incubated with goat anti-rabbit IgG conjugated with peroxidase. After washing the sample three times with phosphate buffered saline following secondary antibody staining, the samples were immersed in diaminobenzidine-$H_2O_2$ (2 mg/ml diaminobenzidine, 0.02% $H_2O_2$ in 0.02 M phosphate buffer) solution for 15 minutes. The samples were washed with phosphate buffered saline. The stained vascular endothelial cells in the grafts (N=17) and control groups (N=14) were counted using a light microscope at 200× magnification. The result was expressed as number of blood vessels/field area (0.8 mm$^2$).

The hearts were fixed in 1% glutaraldehyde in phosphate buffer. The samples were postfixed with 1% osmium tetroxide, dehydrated in graded ethanol (50, 70, 90 and 100%), polymerized in propylene oxide at 60° C. overnight, sectioned, and scoped in a JEOL 1200 TEM electron microscope (10).

EXAMPLE 7

Cell Grafts

Cultured cardiomyocytes, smooth muscle cells, endothelial cells, and/or fibroblasts were seeded on the biological mesh, such as a collagen membrane, and non-biological membranes, such as non-degradable membranes (Dacron) or degradable membranes (polyglycolic acid polymers). The mesh and the cells were cultured in the cell culture medium. At 7 days after culture, the mesh was fixed in 2% formaldehyde and 2% glutaraldehyde in phosphate buffer (0.15 M NaCl and 0.015 M $NaH_2PO_4$, pH 7.2) at 4° C. for 12 hours. The mesh with cells was embedded in paraffin and sectioned into 10 μm thick slices. The sections were stained with haematoxylin and eosin as described in Example 5, and photographed.

EXAMPLE 8

Cell Gluing Technique for Cell Transplantation

To be successful in preventing failure of the infarcted heart, sufficient cardiomyocytes must be implanted into the infarcted myocardium. Although this can be done by multiple syringe injections, injecting the cells, unfortunately, limits the number of cells which can be transplanted into myocardial scar tissue. We have investigated another technique to apply a large number of cells onto the infarcted myocardium. Thrombin and cryoprecipitate (fibrin glue) derived from human blood clots quickly. Our in vitro results showed survival and contraction of cardiomyocytes in the clot. We used this fibrin glue for cell transplantation.

1. Gluing Injection Site to Prevent Transplanted Cells Leakage: The biological glue can be applied onto the injection site. The injection needle is withdrawn after the glue clots. In such manner, leakage of transplanted cells, as discussed previously, is prevented.
2. Glue the Cells onto the Myocardial Scar Tissue to Prevent Injection Damage: We removed the epicardium of normal myocardium over the scar and damaged myocardium. The transplanted cells were suspended in thrombin. The thrombin with the cells was applied onto the myocardial scar tissue with cryoprecipitate. The glue adhered the cell suspension onto the surface of both the scarred and normal myocardium, and then the pericardium was glued on top of the fibrin clot. Cell loss was prevented. We found that glued cardiomyocytes can survive on the myocardial scar tissue and permit a large number of cells to be transplanted. This technique improved heart function better than only injecting the cells. The cardiomyocytes glued onto the myocardium without epicardium can connect with host cardiomyocytes and allow the transplanted cardiomyocytes to contract synchronously with the host myocardium.
3. Glue the Cellular Mesh onto the Myocardial Scar Tissue to Prevent Its Expansion: Cell grafts comprising biological or non-biological mesh having cells suspended thereon (as described in Example 7) were glued onto the scar tissue. The pericardium was in turn glued on top of the mesh.

EXAMPLE 9

Data Analysis

Data are expressed as the mean±standard error. The Statistical Analysis System software was used for all analysis (SAS Institute, Cary, N.C.). Comparisons of continuous variables between more than two groups were performed by a one-way analysis of variance. If the F ratio was significant from the analysis of variance, a Duncan's multiple-range t test was employed to specify differences between the groups. Alpha for these analyses was set at $p<0.05$.

Function data were evaluated for the sham, control and transplant groups by an analysis of covariance using intracavitary balloon volume as the covariate and systolic, diastolic and developed pressure as dependent variables. Main effects were group, volume, and the interaction between group×volume. If there was an overall difference in the analysis of covariance, multiple pair-wise comparisons were performed to specify which groups were different. Because there were multiple pair-wise comparisons, a Bonferroni correction was performed and the critical alpha level was set at 0.01 for the analysis of covariance.

EXAMPLE 10

Use of Growth Factors in Treating Idiopathic Hypertorphic Cardiomyopathy (HCM)

Idiopathic hypertrophic cardiomyopathy (HCM) is a primary cardiac abnormality characterized by regional asymmetrical myocardial hypertrophy. The hypertrophic myocardium can result in obstruction of left ventricular ejection as well as systolic and diastolic dysfunction and myocardial ischemia. Symptoms unresponsive to medical therapy can necessitate surgery.

HCM is described for the most part as a heterogeneous disease of the sarcomeres. At least 34 missense mutations have been described in the β-myosin heavy chain gene, 7 mutations in the candidate loci also exist. However, family studies suggest that the autosomal dominant trait accounts for only 50% of HCM patients. The remaining HCM patients show no familial transmission and the disease occurs sporadically. Myocardial calcium kinetics and sympathetic stimulation have been studied because of diastolic functional abnormalities. However, none of these findings explains the regional myocardial hypertrophy (cardiomyocyte hypertrophy and over synthesis of extracellular matrix proteins) observed in most HCM patients. The etiology of this disease remains unknown. It is thought that growth factors may play an important role in cardiomyocyte proliferation, cell hypertrophy and the overproduction of extracellular matrix.

To investigate the involvement of growth factors on myocardial hypertrophy in HCM patients, we evaluated gene expression and cellular localization of transforming growth fact β1 (TGFβ1), insulin-like growth factors (IGF-I, -II) and platelet-derived factor-B (PDGF-B) in ventricular biopsies obtained from patients with HCM (N=8), aortic stenosis (AS, N=8), stable angina (SA, N=8) and explained hearts with ischemic cardiomyopathy (TM, N=7).

Methods: Levels of TGFβ1, IGF-I, IGF-II and PDGF-B transcripts were quantitated using multiplex RT-PCR. Glyceraldehyde 3-phosphate dehydrogenase (G3PDH) was used as an internal standard. Antibodies against TGFβ1 and IGF-I were used to localize their peptides within the myocardium. Antisense and sense (control) cRNA probes of TGFβ1 and IGF-I, labeled with digoxigenin, were used to localize the growth factor transcripts by in situ hybridization.

Results: mRNA levels (densitometric ratio of GF/G3PDH) of TGFβ1 and IGF-I in HCM (0.75±0.05, 0.85±0.15, mean±ISE) were significantly ($p<0.01$ for all groups) elevated in comparison to non-HCM myocardium (AS: 0.38±0.07, 0.29±0.06; SA: 0.32±0.04, 0.18±0.05; TM: 0.25±0.03, 0.15±0.03). mRNA level of TGFβ1 and IGF-I in the hypertrophic AS myocardium were greater (p=0.02, p=0.05) than those in the explained myocardium (TM). Immunohistochemical and in situ hybridization studies showed increased expression of TGFβ1 and IGF-I in the HCM cardiomyocytes.

Conclusion: Gene expression of TGFβ1 and IGF-I was enhanced in idiopathic hypertrophy and may be associated with its development.

B. Results

1. Ventricular and Atrial Cardiomyocytes: Fetal and adult mammalian ventricular cardiomyocytes and adult mammalian atrial cardiomyocytes were isolated using enzymatic digestion as described above. After purification, the purity of the cultured ventricular and atrial cardiomyocytes was greater than 94% (N=8) as determined by the percentage of cells which stained for cardiac myosin heavy chain. The cardiomyocytes grew in vitro, connected with each other and formed a tissue pattern after six days of culture. The fetal cardiac-like tissues contracted regularly and spontaneously in culture. The adult cardiomyocytes did not contract in culture.

2. Smooth Muscle Cells: Fetal and adult smooth muscle cells were successfully cultured. The cells proliferated in the culture. The cultured cells were stained strongly with antibodies against α-smooth muscle actin.

3. Vascular Endothelial Cells: Endothelial cells were isolated from blood vessel and cultured. Staining with antibody against factor VIII, more than 95% cells in the culture dish were endothelial cells.

4. Fibroblasts: Fetal and adult skin fibroblasts were isolated and cultured. The cells proliferated in the culture condition. When the culture reached confluency, the cells formed a typical fibroblast pattern: spindle-shape cell and wave pattern.

5. Cell Transfection: Twenty-four hours after transfection of freshly isolated cells, the percentage of the transfected cells with β-galactosidase was 18.2±5.2% (N=6). No cells stained positively in the control groups with plasmid pREP4 (N=6) and without a plasmid (N=6). After culturing for 4 weeks, 5.4±3.1% (N=6) of the transfected cells stained positively for β-galactosidase activity.

6. Myocardial Scar Tissue: Immediately after myocardial injury, 25±3% of the left ventricular free wall (LVFW) was transmurally damaged. The cardiomyocytes were fragmented. At one week, most of the necrosed cardiomyocytes were gone and a predominantly mononuclear inflammatory infiltrate was present in the affected area. At two weeks the inflammatory infiltrate had almost disappeared and fibroblasts and collagen deposition were evident. At four and eight weeks, the scar was composed of fibrotic tissue. The tissue was less cellular and lymphocytes were not observed. No cardiac muscle cells were observed in any scar tissue.

The myocardial scar of the left ventricle increased in size over the 8 week study period in the control hearts. Although the scar sizes at 1 and 2 weeks (13±6% and 21±4% of left ventricular free wall) were not statistically different, the scar size after 4 weeks (39±5% of left ventricular free wall) was greater ($p<0.01$). At 8 weeks there was a further increase ($p<0.01$) in scar size (55±3% of left ventricular free wall).

7. Optimal Time for Cell Transplantation: The fetal rat cardiomyocytes transplanted into myocardial tissue immediately after myocardial damage did not survive in the affected area. The scar area (53±5%) of transplanted hearts was similar to that of the control group 55±3% of the left ventricular free wall). Cardiomyocytes transplanted at 2 weeks after myocardial damage formed cardiac tissue which occupied 34% of the total scar area (11±3% of the left ventricular free wall). Similarly cardiomyocytes transplanted at 4 weeks occupied 32% of total scar area (14±4% of left ventricular free wall). The scar sizes for both the 2 and 4 week transplanted hearts were smaller ($p<0.01$) than the scar size of the control hearts. The scar size of the hearts transplanted at 2 weeks was smaller ($p<0.01$) than that of the hearts transplanted at 4 weeks.

8. Transplanted Cells in Myocardial Scar Tissue: At four or six weeks post ventricular cardiomyocyte transplantation, only the fetal cardiomyocyte tissue (N=17) had formed within the myocardial scar tissue. The cells were connected to each other and formed a cardiac tissue pattern. The tissue of all 3 animals, transplanted with cardiomyocytes transfected with the β-galactosidase gene, contained β-galactosidase activity. The transplanted cardiomyocytes contained sarcomeres and were connected by junctions composed of desmosomes and fascia adherens, which were not present in the cardiomyocytes immediately prior to transplantation. Lymphocytic infiltration surrounded the cardiac tissue formed by transplanted fetal cardiomyocytes. In the control animals (N=14), cardiac tissue, lymphocytic infiltration, and β-galactosidase activity were not observed in the scar. The scar was less cellular than the four-week old scar tissue.

Adult rat atrial cardiomyocytes were autotransplanted into the scar tissue of the same rat. At 6 weeks after transplantation, the transplanted cells were observed in the myocardial scar tissue which were identified by the specific antibody against cardiac myosin heavy chain. There was no lymphocytic infiltration. No cardiac tissue was found in the scar tissue of control rate.

At 6 weeks after transplantation, both allo- and auto-smooth muscle cells transplanted scars contained smooth muscle tissue which stained positively for α-smooth muscle actin. The allotransplant were infiltrated with lymphocytes indicative of immuno-rejection. There was no lymphocytic infiltrate or signs of immunorejection in the auto-smooth muscle cell transplant.

At 6 weeks after transplantation, the transplanted fibroblasts proliferated in the myocardial scar tissue. The cells secreted extracellular matrix, which increases the thickness of the scar tissue. The transplanted cells also stimulated angiogenesis, which survived damaged myocardial tissue in the scar tissue. There were no cardiac muscle cells in the scar tissue in control animals. The scar tissue at left ventricular free wall of the control hearts dilated during systole while the transplanted scar was immobile. Although the surface area of the transplanted scar(22.9±6.2 mm$^2$) was similar to that of the control scar (23.8±6.5 mm$^2$), the scar thickness (1.9±0.9 mm, N=12) of the transplanted hearts was twice (p<0.01) that of the control hearts (1.0±0.4 mm, N=10). Consistent with the above findings, the left ventricular volume of the transplanted hearts was 275±48 mm$^3$ (N=12) which was less (p<0.01) than the 360±94 mm$^3$ volume of the control hearts (N=10).

Although a detailed observation was not made of transplanted endothelial cells, staining with antibody against factor VIII found that more cells stained positively in scar tissue with transplanted endothelial cells than with the control scar tissue.

9. Angiogenesis in Myocardial Scar Tissue after Cell Transplantation: At 4 to 6-weeks after transplantation angiogenesis occurred in the transplanted fetal ventricular cardiomyocyte transplant as assessed by histology and electron microscopy. Significantly more arterioles and venules were found (p<0.01) in the cardiomyocyte grafts (1.2±0.6 vessels/ 0.8 mm$^2$, N=14) than in the control myocardial scar tissue (0.1±0.1 vessels/0.8 mm$^2$, N=14).

Similarly angiogenesis occurred in the atrial cell, endothelial cell, smooth muscle cell and fibroblast cell transplants.

10. Transplanted Cells Limited Scar Expansion: At 4 to 6 weeks after transplantation of the cells, the heart rate and coronary flow did not differ among the sham, control and transplanted animals. The control myocardial wall at the site of injury had thinned and consisted of fibrous tissue and a few blood vessels. No cardiac muscle or lymphocytes were present. The control and transplanted hearts were larger (p<0.01) than the sham hearts. At 4 weeks after cryo-injury, 36.4±4.4% (mean±1SE, N=5) of the left ventricular free wall in the pretransplant animals was replaced with a transmural scar. At 8 weeks, the scar tissue expanded (p<0.01) in the control group to 54.6±2.9% (N=5) of the free wall for the fetal cardiomyocytes. The scar tissue in the transplanted animals was 43.4±1.8% (N=5) of the left ventricular free wall. This did not significantly differ from the pretransplanted animals at 4 weeks after cryo-injury and was less (p<0.05) than the control hearts at 8-weeks after cryo-injury. The transplanted cardiomyocytes formed cardiac tissue which occupied 36.5±3.5% (N=5) of the scar tissue. The transplanted tissue visibly contracted. We were unsuccessful in measuring its contractility because of the contractions of the heart. After removing the hearts and separating the scar area, the transplanted region continued to contract when stimulated.

Similarly the atrial cell, smooth muscle cell, and fibroblast transplants limited scar expansion.

11. Improvement of Heart Function by Transplanted Cell: Ventricular function in the transplanted and the control hearts into which cells were transplanted immediately after myocardial injury was no different. Analysis of covariance demonstrated no interaction between balloon volume and treatment group for developed pressures. Ventricular function of the transplanted and the control hearts when the cardiomyocytes were transplanted at 2 weeks after myocardial injury was different because an analysis of covariance demonstrated a significant (p<0.05) interaction between balloon volume and treatment group for developed pressures. The transplanted hearts had better (p<0.05) function than the control hearts. Similarly cells transplanted at 4 weeks after myocardial necrosis improved (p<0.05) myocardial function. The hearts transplanted at 2 weeks had higher (p<0.05, p<0.05, p<0.05) developed pressures at balloon volumes 0.1, 0.2, and 0.3 ml than hearts transplanted at 4 weeks.

In the measurement of ventricular function in the sham-operated, the transplanted and the control hearts, an analysis of covariance demonstrated a significant (p<0.05) interaction between balloon volume and treatment group for systolic, diastolic and developed pressures. Pairwise comparisons demonstrated a significant (p<0.05) depression in systolic and developed pressure in control animals compared to the sham-operated normal hearts. The transplanted hearts had better (p<0.05) function than the control hearts although both systolic pressure and developed pressure were lower (p<0.05) than the sham-operated normal hearts. Diastolic pressures were significantly lower in both the cryo-injured controls and the transplanted hearts than sham-operated normal hearts at higher balloon volumes due to the marked dilatation resulting from myocardial scar expression.

12. Tissue Engineered Graft: In the mesh, cardiomyocytes, smooth muscle cells, fibroblats, and endothelial cells were observed. The tissue which formed in the mesh stained strongly with haematoxylin and eosin.

C. Summary

From the above results, it can be seen that we have transplanted muscle and non-muscle cells in the scar tissue. These cells formed tissue, altered structure of the scar, improved heart function, stimulated angiogenesis, and expressed a gene foreign to the scar. From these results, the following conclusions are drawn:

1. Cultured adult atrial cardiomyocytes could be successfully transplanted into the scar. The atrial tissue could be digested and the atrial cells immediately transplanted or the atrial tissue could be digested, cultured and passaged up to five times and then transplanted. Auto- and allo-transplantation of cultured adult atrial cardiomyocytes formed tissue within the scar. Heart function improved. Angiogenesis occurred. No immunorejection occurred with auto-transplantation of the adult atrial cardiomyocytes.

2. Smooth muscle cells can be successfully auto- or allo-transplanted into the scar. Smooth muscle tissue formed within the scar. No immunorejection occurred with the auto-transplantation. Angiogenesis occurred. Heart function improved. The cells can be freshly isolated, or cultured and passaged before transplanting.

3. Fibroblasts can be successfully transplanted into scar tissue. Scar thickness increased. Heart function improved. Angiogenesis occurred. Host cardiomyocytes survived in the scar. The cells can be freshly isolated, or cultured and passaged before transplanting.

4. The addition of cryo-precipitate to the injection site prevented leakage of the transplanted cells from the scar.

5. A plasmid containing a foreign gene to the scar tissue and heart tissue was transfected into the cultured cells to be transplanted. The cells were successfully transplanted into the scar tissue and expressed the foreign gene.

6. Cardiomyocytes, smooth muscle cells, skeletal muscle cells, fibroblasts, and endothelial cells can be successfully transplanted into fibrous membranes and non-degradable or biodegradable polymers to form tissue. The product of such a process would be a patch which can have various clinical and therapeutic uses. Such membranes may be made from Dacron or biodegradable sheets such as polyglycolic acid polymers with or without polylactic acid polymers. Such a patch can be associated with a pacemaker and be implanted close to a cardiac defect thereby providing a means of paced cardiomyoplasty.

7. Cell combinations could be successfully transplanted to form tissue within a scar to improve function, to stimulate angiogenesis and to form tissue.

8. The optimal time for transplantation is immediately after the acute inflammatory response to the myocardial injury has disappeared.

9. Adult mammalian atrial and ventricular cardiomyocytes can be successfully isolated from human myocardium, cultured, passaged and stored using the cell culture procedure described for human cardiomyocytes described in the Human Cell Isolation, Culturing and Storage section. Human cardiomyocytes can be prepared for long term storage in liquid nitrogen and thawed for culturing as described. Such cultured cells can then be used in forming grafts as discussed above.

10. The biological glue technique used in the cell transplantation procedure increased the number of cells transplanted in myocardial scar tissue. This invention enhanced the transplant success rate and maximized the improvement of heart function.

Co-transplantation of growth factors such as IGF-I, IGF-II, TGF-β1 and PDGF-B increased the survival of transplanted cells, induces transplanted muscle hypertrophy, and stimulates angiogenesis. Based on these findings, the use of other growth factors such as fibroblast growth factor and vascular endothelial growth factor are also possible. such growth factors can be co-transplanted either alone or in combination. These techniques can increase transplanted muscle size and survival in myocardial scar tissue and damaged myocardial tissue.

11. Cultured cells can be employed to restore regional cardiac function and blood flow to regions in the heart damaged by acquired disease processes or absent because of congenital defects. During reconstructive surgery, the defective portion of the heart is removed and replaced with inert materials to secure a water-tight seal. Attaching a contracting tissue of myocytes to the reconstruction patch will permit the return of function to the destroyed region. Implantation of a collection of cells could restore function and improve the quality of life of the patients undergoing reconstructive surgery.

12. Most acquired or congenital cardiac defects are closed with inert materials intended to provide a water-tight seal. Instead of an inert material, a graft consisting of a biodegradable or non-biodegradable scaffolding supporting cultured cells can be employed to close such cardiac defects. The graft would employ myocytes enhanced with genes to increase perfusion and contractility (by increasing the size and number of myocytes). In addition, the endothelial cells can be applied to the blood surface of the graft to prevent intravascular clot formation in the heart. The endothelial cells could be genetically engineered so that they produce proteins that prevent clot formation on the blood surfaces. The cellular grafts will permit closure of acquired and congenital cardiac defects with functioning tissue which may improve heart function.

13. Cardiac surgeons frequently remove segments of the heart which have been damaged or are defective due to congenital abnormalities. A cellular graft permits an opportunity to restore function to regions which are usually closed with inert materials. The graft may consist of myocytes grown on biodegradable scaffolding. Endothelial cells can be grown on the blood interface layer. The cells will create a functioning graft which will replace the region removed at the time of surgery. The functioning myocardial graft could restore function of patients who have suffered a myocardial infarction and require removal of the destroyed regions. The functioning graft could re-establish systematic and/or pulmonary circulation for patients with extensive congenital defects undergoing reconstructive surgery. A functioning myocardial graft offers the promise of restoring an improved quality of life to disabled individuals.

Although the invention has been described with reference to certain specific embodiments, various modifications thereof will be apparent to those skilled in the art without departing from the spirit and scope of the invention as outlined in the claims appended hereto.

REFERENCES

1. Tompson L. Fetal transplants show promise. *Science*. 1992;257:868–870.
2. Gussoni E, Pavlath G. K., Lanctot A. M., Sharma K. R., Miller R. G., Steinman L., Blan H. M. Normal dystrophin transcripts detected in Duchenne muscular dystrophy patients after myoblast transplantation. *Nature*. 1992;356:435–438.
3. Koh G. Y., Klug M. G., Soonpaa M. H., Field L. J. Differentiation and long-term survival of C2C12 myoblast grafts in heart. *Journal of Clinical Investigation*. 1993;92:1548–54.
4. Soonpaa M. H., Koh G. Y., Klug M. G., Field L. J. Formation of nascent intercalated disks between grafted fetal cardiomyocytes and host myocardium. *Science*. 1994;264:98–101.
5. Li R. K., Mickle D. A. G., Weisel R. D., Zhang J., Mohabeer M. K. In vivo survival and function of transplanted rat cardiomyocytes. *Circulation Research*. 1996;78:283–288.
6. Li R. K., Jia Z. Q., Weisel R. D., et al. Cardiomyocytes transplantation improves heart function *Annals of Thoracic Surgery*. 1996;62:654–661.
7. Li R. K., Weisel R. D., Williams W. G., Mickle D. A. G. Method of culturing cardiomyocytes from human pediatric ventricular myocardium. *Journal of Tissue Culture and Methodology*. 1992;14:93–100.
8. Mickle D. A. G., Li R. K., Weisel R. D., Tumiati L. C., Wn T. W.: Water-soluble antioxidant specificity against free radical injury using cultured human ventricular myocytes and fibroblasts and saphenous vein endothelial cells. *Journal of Molecular and Cell Cardiology* 1990;22:1297–1304.
9. Simpson P., McGrath A., Savion S. Myocyte hypertrophy in neonatal rat heart cultures and its regulation by serum and by catecholamines. *Circulation Research* 1982;51:787–801.
10. Li R. K., Mickle D. A. G., Weisel R. D., et al. Human pediatric and adult ventricular cardiomyocytes in culture: assessment of phenotypic changes with passaging. *Cardiovascular Research*. 1996;32:362–73.
11. Shi Q. W., Li R. K., Mickle D. A. G., Jackowski G. Analysis of the upstream regulatory region of human ventricular myosin light chain one gene. *Journal of Molecular and Cell Cardiology*. 1992;24:1221–1229.
12. Stephen S. E., Furukawa R. D., Zhang J., Li R. K., Tumiati L. C., Weisel R. D., Mickle D. A. G.: Cardiac storage with University of Wisconsin solution and a nucleoside-transport blocker. *Annals of Thoracic Surgery*. 1995;59:1127–1133.
13. Pfeffer J. M., Pfeffer M. A., Fletcher P. J., Braunwald E. Progressive ventricular remodeling in rat with myocardial infarction. *American Journal of Physiology*. 1991;260:H1406–14.
14. Jugdutt B. I., Khan M. I. Effect of prolonged nitrate therapy on left ventricular remodelling after canine acute myocardial infarction. *Circulation*. 1994;89:2297–307.

15. Wu T. W., Wu J., Zeng L. H., Sugiyama H., Mickle D. A. G., Au JX. Reduction of experimental myocardial infarct size by infusion of lactosylphenyl Trolox. *Cardiovascular Research*. 1993;27:736–39.
16. Li, R. K., Mickle, D. A. G., Weisel, R. D., et al., Optimal time cardiomyocyte transplantation to maximize myocardial function after left ventricular necrosis. Submitted to Circulation Research; not yet published.

The embodiments of the invention in which an exclusive property or privilege is claimed are defined as follows:

1. A method of forming a stable myocardial graft in a mammal, the method comprising transplanting, into scar tissue in a heart, cells chosen from the group consisting of:
   adult cardiomyocytes;
   adult fibroblasts;
   fetal fibroblasts;
   smooth muscle cells;
   endothelial cells; and
   skeletal myoblasts.

2. The method as claimed in claim 1 wherein said cells are chosen from adult or fetal smooth muscle cells and fibroblasts.

3. The method of claimed in claim 1, wherein the adult cardiomyocytes comprise atrial cardiomyocytes.

4. The method as claimed in claim 1, wherein said graft comprises auto-, allo- or xenotransplanted cells.

5. The method as claimed in claim 1, wherein said graft comprises autotransplanted adult cardiomyocytes.

6. The method as claimed in claim 5, wherein said adult cardiomyocytes comprise atrial cardiomyocytes.

7. The method as claimed in claim 1, wherein said cells are directly introduced into said scar tissue.

8. The method as claimed in claim 7, wherein said cells are introduced into said scar tissue by injection.

9. The method as claimed in claim 8, wherein the injection site is sealed with a biological adhesive to prevent leakage of said cells.

10. The method as claimed in claim 1, wherein said cells are attached to a biodegradeable or non-degradable mesh.

11. The method as claimed in claim 1, wherein said cells are transfected to deliver recombinant molecules to said scar tissue.

12. The method as claimed in claim 1, wherein said cells are used in myocardial reconstructive surgery.

13. The method as claimed in claim 1, wherein said cells are attached to the outer surface of said myocardial or scar tissue with a biological adhesive.

14. The method as claimed in claim 1, wherein said cells are transplanted following an inflammatory response in said myocardial tissue.

15. The method as claimed in claim 1, wherein growth factors are co-transplanted with said cells.

16. The method as claimed in claim 15, wherein said growth factors are chosen from the group consisting of: insulin-like growth factors I and II; transforming growth factor-β1; platelet-derived growth factor-B; basic fibroblast growth factor; and, vascular endothelial growth factor.

17. A therapeutic graft for application in mammalian scar tissue in a heart, the graft comprising transplanted cells chosen from the group consisting of:
   adult cardiomyocytes;
   adult fibroblasts;
   fetal fibroblasts;
   smooth muscle cells;
   endothelial cells; and
   skeletal myoblasts.

18. The graft as claimed in claim 17 wherein said transplanted cells are chosen from smooth muscle cells and fetal fibroblasts.

19. The graft as claimed in claim 17, wherein the adult cardiomyocytes comprise atrial cardiomyocytes.

20. The graft as claimed in claim 17, wherein said graft comprises auto-, allo- or xenotransplanted cells.

21. The graft as claimed in claim 17, wherein said graft comprises autotransplanted adult cardiomyocytes.

22. The graft as claimed in claim 21, wherein said adult cardiomyocytes comprise atrial cardiomyocytes.

23. The graft as claimed in claim 17, wherein said cells are introduced into said scar tissue by injection.

24. The graft as claimed in claim 17, wherein said cells are transfected to deliver recombinant molecules to said scar tissue.

25. The graft as claimed in claim 17, further comprising growth factors.

26. The graft as claimed in claim 25, wherein said growth factors are chosen from the group consisting of: insulin-like growth factors I and II; transforming growth factor-β1; platelet-derived growth factor-B; basic fibroblast growth factor; and, vascular endothelial growth factor.

27. The graft as claimed in claim 17, wherein said cells are attached to a biodegradable mesh.

28. A therapeutic graft, for implantation in mammalian scar tissue in a heart, comprising biodegradable or non-biodegradable scaffolding supporting cells, said cells being chosen from the group consisting of:
   adult cardiomyocytes;
   adult fibroblasts;
   fetal fibroblasts;
   smooth muscle cells;
   endothelial cells; and
   skeletal myoblasts.

29. The graft of claim 28, wherein said scaffolding comprises Dacron or polyglycolic acid polymers with or without polylactic acid polymers.

30. The graft of claim 28, wherein said cells are cardiomyocytes, smooth muscle cells or endothelial cells.

31. The graft of claim 28, wherein said graft further includes an implantable pacemaker.

32. A method of storing cultured cardiomyocytes isolated from pediatric mammalian myocardial tissue, said method comprising the steps of:
   a) dissociating cultured cardiomyocytes from a culture plate using sub-culturing enzyme solution, said sub-culturing enzyme solution comprising 0.01% trypsin, 0.02% glucose, and 0.5 mM EDTA;
   b) adding culture medium, said culture medium comprising Iscove's modified Dulbecco's medium (IDMD), 10% fetal bovine serum, and, 0.1 mM β-mercaptoethanol, wherein said culture medium is in a ratio of 5 volumes of culture medium to 1 volume of said sub-culturing enzyme solution;
   c) centrifuging the solution at 581×g for 5 minutes;
   d) discarding the supernatant and re-suspending the pellet in 1 mL IMDM containing 20% fetal bovine serum and 20% glycerol; and,
   e) freezing and storing the resulting suspension in liquid nitrogen.

33. The method of claim 32 further including thawing the frozen sample at 37° C. for 3 to 5 days in a solution of IMDM containing 20% fetal bovine serum.

34. A method of storing cultured cardiomyocytes isolated from adult mammalian myocardial tissue, said method comprising the steps of:
- a) dissociating cultured cardiomyocytes from a culture plate using sub-culturing enzyme solution, said sub-culturing enzyme solution comprising 0.01% trypsin, 0.02% glucose, and 0.5 mM EDTA;
- b) adding culture medium, said culture medium comprising Iscove's modified Dulbecco's medium (IMDM), 10% fetal bovine serum, and, 0.1 mM β-mercaptoethanol, wherein said culture medium is in a ratio of 5 volumes of culture medium to 1 volume of said sub-culturing enzyme solution;
- c) centrifuging the solution at 581×g for 5 minutes;
- d) discarding the supernatant and re-suspending the pellet in 1 mL IMDM containing 20% fetal bovine serum and 20% glycerol; and,
- e) freezing and storing the resulting suspension in liquid nitrogen.

35. The method of claim 34 further including thawing the frozen sample at 37° C. for 3 to 5 days in a solution of IMDM containing 20% fetal bovine serum.

36. A method of treating defective, damaged or scarified heart tissue comprising transplanting into said scarified heart tissue a graft of cells chosen from the group consisting of:
adult cardiomyocytes;
adult fibroblasts;
fetal fibroblasts;
smooth muscle cells;
endothelial cells; and
skeletal myoblasts.

37. The method as claimed in claim 36 wherein said cells are directly introduced into said scarified heart tissue.

38. The method as claimed in claim 37 wherein said graft is a patch comprising said cells attached to a biologically acceptable biodegradable or non-degradable scaffolding.

39. The method as claimed in claim 38 comprising the steps of: (a) surgically removing defective heart tissue thereby creating an opening; and, (b) attaching said graft to said opening to form a water tight seal.

40. The method of claim 36, wherein said graft is used for cardiomyoplasty.

41. The method of claim 36, wherein said graft is used for closing cardiac defects.

42. The method of claim 36, wherein said graft is used for myocardial reconstructive surgery.

43. A method of forming a stable myocardial graft in a mammal, the method comprising transplanting, into myocardial tissue in a heart, cells chosen from the group consisting of:
group fibroblasts;
fetal fibroblasts;
smooth muscle cells; and
endothelial cells.

44. A therapeutic graft for application in mammalian myocardial tissue in a heart, the graft comprising transplanted cells chosen from the group consisting of:
adult fibroblasts;
fetal fibroblasts;
smooth muscle cells; and
endothelial cells.

45. A therapeutic graft, for implantation in mammalian myocardial tissue in a heart, comprising biodegradable or non-biodegradable scaffolding supporting cells, said cells being chosen from the group consisting of:
adult fibroblasts;
fetal fibroblasts;
smooth muscle cells; and
endothelial cells.

* * * * *

(12) EX PARTE REEXAMINATION CERTIFICATE (5453rd)
United States Patent
Mickle et al.

(10) Number: US 6,110,459 C1
(45) Certificate Issued: Jul. 18, 2006

(54) TRANSPLANTS FOR MYOCARDIAL SCARS AND METHODS AND CELLULAR PREPARATIONS

(75) Inventors: Donald A. G. Mickle, Toronto (CA); Ren-Ke Li, Scarborough (CA); Richard D. Weisel, Toronto (CA)

(73) Assignee: Genzyme Corporation, Cambridge, MA (US)

Reexamination Request:
No. 90/006,237, Mar. 6, 2002

Reexamination Certificate for:
Patent No.: 6,110,459
Issued: Aug. 29, 2000
Appl. No.: 08/863,882
Filed: May 28, 1997

(51) Int. Cl.
*A01N 63/00* (2006.01)
*A01N 65/00* (2006.01)
*A61K 48/00* (2006.01)
*C12N 5/00* (2006.01)
*C12N 5/08* (2006.01)

(52) U.S. Cl. .......... 424/93.21; 424/93.1; 424/93.2; 435/371; 435/373; 435/374; 435/375

(58) Field of Classification Search .......... 424/93.1, 424/93.2, 93.21; 435/371, 373, 374, 395
See application file for complete search history.

(56) References Cited

U.S. PATENT DOCUMENTS 4,963,489 A * 10/1990 Naughton et al. .......... 435/1.1
5,543,318 A    8/1996 Smith et al. .......... 435/240.2

OTHER PUBLICATIONS

Leor et al. Circulation 94 (Suppl II): II332–II336, 1996.*
Kao et al, Satellite Cells For Myocardial Regeneration, 1989, Physiologist, 32:220.
Kao et al., Muscle Regeneration of Injured Myocardium, 1991, J. Cell Biochem. suppl., 15C:73, F 420.
Marelli et al., Satellite Cell Implantation for Neo–Myocardial Regeneration, Cell Transplantation, vol. I, ( First International Congress of The Cell Transplant Society May 31 – Jun. 3, 1992) Cell Transplantation, 1:89–234, No. 197.
Marelli et al., Cell Transplantation For Myocardial Repair: An Experimental Approach, 1992, Cell Transplant., 1:383–390.
Chiu et al., Cellular Cardiomyoplasty: Myocardial Regeneration With Satellite Cell Implantation, 1995, Ann. Thorac. Surg., 60:12–18.
Yoon et al., Transplanting Satellite Cells into Damaged Myocardium, 1995, Tex. Heart Inst. J., 22:119–125.
Murry et al., Skeletal and Cardiac Myoblast Transplantation after Myocardial Necrosis; Possible Routes to Muscle Regeneration 1995, Circulation, 92:I12a.
Murry et al., Skeletal Myoblast Transplantation for Repair of Myocardial Necrosis, 1996, J. Clin. Invest., 98(11):2512–2523.
Jacobson et al., Cell Cultures of Adult Cardiomyocytes as Models of the Myocardium, 1986, J. Mol. Cell. Cardiol., 18:661–678.
Kruppenbacher et al., Cardiomyocytes of Adult Mice in Long–Term Culture, 1993, Naturwissenshcaften, 80:132–134.
Metzger et al., Regenerative Capacity of Transplanted Cardiac Muscle in the Rat, 1986, Acta Anat., 125:180–182.

* cited by examiner

*Primary Examiner*—Q. Janice Li
(74) *Attorney, Agent, or Firm*—Robert J. Cobert

(57) ABSTRACT

A method is provided for forming a graft in heart tissue which comprises the transplantation of cells chosen from cardiomyocytes, fibroblasts, smooth muscle cells, endothelial cells and skeletal myoblasts. The grafts are especially useful in treating scar tissue on the heart. Also provided is a method of isolating and culturing cardiomyocytes for use in such grafts.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 17–27, 32–35 and 44 are cancelled.

Claims 1, 2, 28–31, 36, 43 and 45 are determined to be patentable as amended.

Claims 3–16 and 37–42, dependent on an amended claim, are determined to be patentable.

1. A method of forming a stable myocardial graft in a mammal, the method comprising transplanting, into scar tissue in a heart, cells chosen from the group consisting of:
   adult cardiomyocytes;
   adult fibroblasts;
   [fetal fibroblasts]
   smooth muscle cells;
   endothelial cells; and
   skeletal myoblasts;
   *wherein said myocardial graft improves heart function in said mammal.*

2. The method as claimed in claim 1 wherein said cells are chosen from adult [or fetal] smooth muscle cells and *adult* fibroblasts.

28. *A method for improving heart function comprising:*
   *implanting a* therapeutic graft[, for implantation in] *into* mammalian scar tissue in a heart, *said therapeutic graft* comprising biodegradable or non-biodegradable scaffolding supporting cells, said cells being chosen from the group consisting of:
   adult cardiomyocytes;
   adult fibroblasts;
   [fetal fibroblasts]
   smooth muscle cells;
   endothelial cells; and
   skeletal myoblasts;
   *wherein said therapeutic graft improves heart function.*

29. The [graft] *method* of claim 28, wherein said scaffolding comprises Dacron or polyglycolic acid polymers with or without polylactic acid polymers.

30. The [graft] *method* of claim 28, wherein said cells are cardiomyocytes, smooth muscle cells or endothelial cells.

31. The [graft] *method* of claim 28, wherein said [graft] *method* futher includes [an implantable] *implanting a* pacemaker.

36. A method of treating defective, damaged or scarified heart tissue comprising transplanting into said scarified heart tissue a graft of cells chosen from the group consisting of:
   adult cardiomyocytes;
   adult fibroblasts;
   [fetal fibroblasts;]
   smooth muscle cells;
   endothelial cells; and
   skeletal myoblasts;
   *wherein said graft improves heart function.*

43. A method of forming a stable myocardial graft in a mammal, the method comprising transplanting, into myocardial tissue in a heart, cells chosen from the group consisting of:
   [group fibroblasts;
   fetal fibroblasts;]
   smooth muscle cells; and
   endothelial cells;
   *wherein said myocardial graft improves heart function in said mammal.*

45. *A method for improving heart function comprising:*
   *implanting a* therapeutic graft[, for implantation in] *into* mammalian myocardial tissue in a heart, comprising biodegradable or non-biodegradable scaffolding supporting cells, said cells being chosen from the group consisting of:
   adult fibroblasts;
   [fetal fibroblasts;]
   smooth muscle cells; and
   endothelial cells;
   *wherein said therapeutic graft improves heart function.*

* * * * *